(12) United States Patent
Weiss

(10) Patent No.: US 6,356,675 B1
(45) Date of Patent: Mar. 12, 2002

(54) FIBER OPTIC REFRACTIVE INDEX MONITOR

(75) Inventor: Jonathan David Weiss, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 928 days.

(21) Appl. No.: 08/566,340

(22) Filed: Dec. 1, 1995

(51) Int. Cl.$^7$ .......................... G02B 6/00; G01N 21/41
(52) U.S. Cl. .................. 385/12; 356/128; 356/132; 356/133; 250/227.14; 250/227.25
(58) Field of Search ............ 385/12, 13; 356/128–137, 356/361; 250/227.11, 227.13, 227.14, 227.16, 227.25

(56) References Cited

U.S. PATENT DOCUMENTS

| | | | | |
|---|---|---|---|---|
| 3,619,068 A | * | 11/1971 | Boreman | 356/130 |
| 3,738,757 A | * | 6/1973 | Barstow | 356/131 |
| 4,050,895 A | | 9/1977 | Hardy et al. | 23/230 R |
| 4,187,025 A | | 2/1980 | Harmer | 356/133 |
| 4,427,293 A | | 1/1984 | Harmer | 356/133 |
| 4,433,913 A | | 2/1984 | Harmer | 356/133 |
| 4,640,615 A | * | 2/1987 | Sasaki | 356/130 |
| 4,711,126 A | * | 12/1987 | Houpt et al. | 73/293 |
| 4,764,671 A | * | 8/1988 | Park | 250/227 |
| 4,824,206 A | | 4/1989 | Klainer et al. | 350/96.29 |
| 4,846,548 A | | 7/1989 | Klainer | 350/96.29 |
| 4,851,817 A | | 7/1989 | Brossia et al. | 340/583 |
| 4,981,338 A | * | 1/1991 | Bobb et al. | 385/12 |
| 5,005,005 A | | 4/1991 | Brossia et al. | 340/604 |
| 5,044,723 A | * | 9/1991 | MacDonald | 385/12 |
| 5,055,699 A | * | 10/1991 | Konig et al. | 356/133 |
| 5,141,310 A | | 8/1992 | Boiarski | 356/133 |
| 5,299,141 A | | 3/1994 | Hungerford et al. | 364/510 |
| 5,305,071 A | * | 4/1994 | Wyatt | 356/128 |
| 5,477,318 A | * | 12/1995 | Ohsaki et al. | 356/136 |
| 5,546,493 A | * | 8/1996 | Noguchi et al. | 385/125 |
| 5,600,433 A | * | 2/1997 | Buttry et al. | 385/12 |

OTHER PUBLICATIONS

Johnathan D. Weiss;, Piezooptic behavior of certain fluids, Applied Optics, vol. 24, p. 1151, Apr. 15, 1985.

* cited by examiner

Primary Examiner—Hemang Sanghavi
(74) Attorney, Agent, or Firm—George H Libman

(57) ABSTRACT

A sensor for measuring the change in refractive index of a liquid uses the lowest critical angle of a normal fiber optic to achieve sensitivity when the index of the liquid is significantly less than the index of the fiber core. Another embodiment uses a liquid filled core to ensure that its index is approximately the same as the liquid being measured.

12 Claims, 4 Drawing Sheets

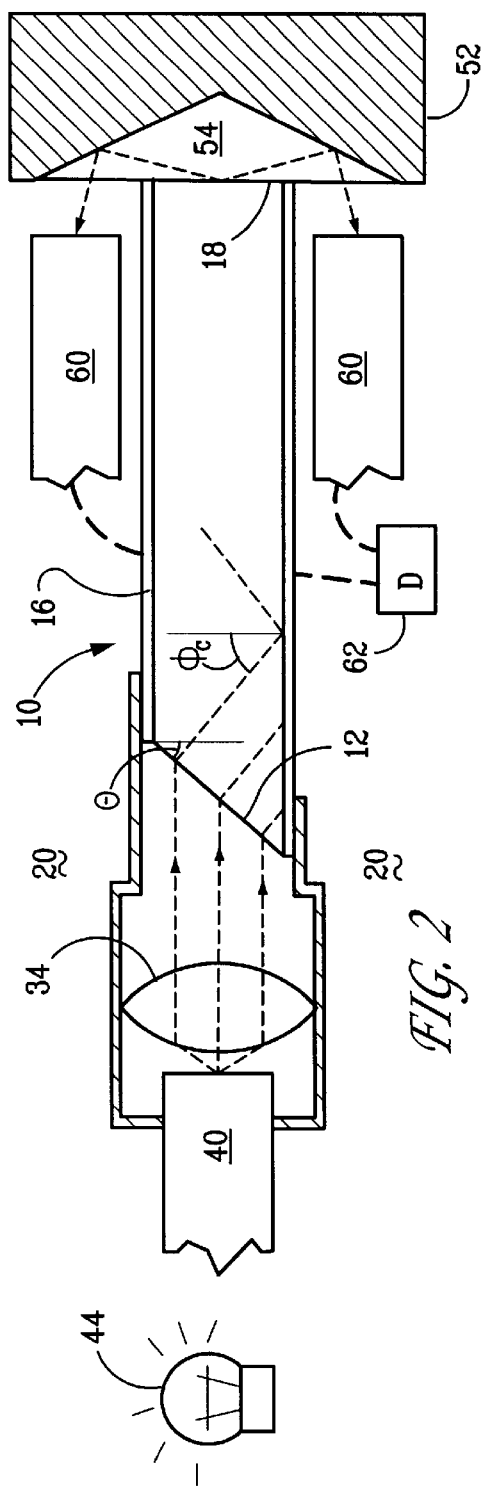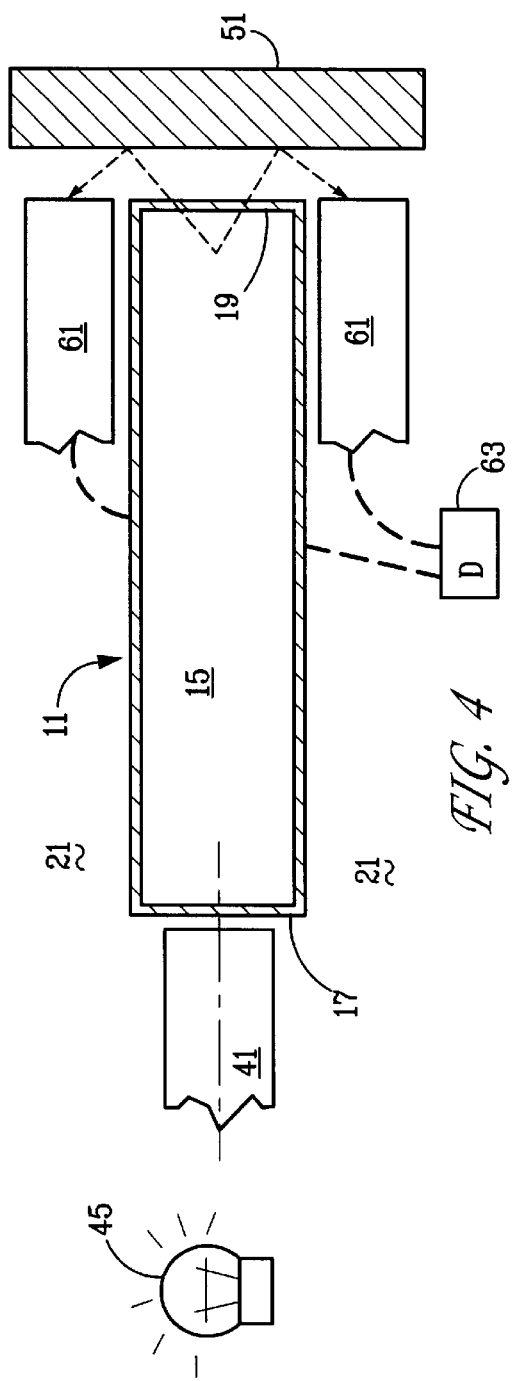

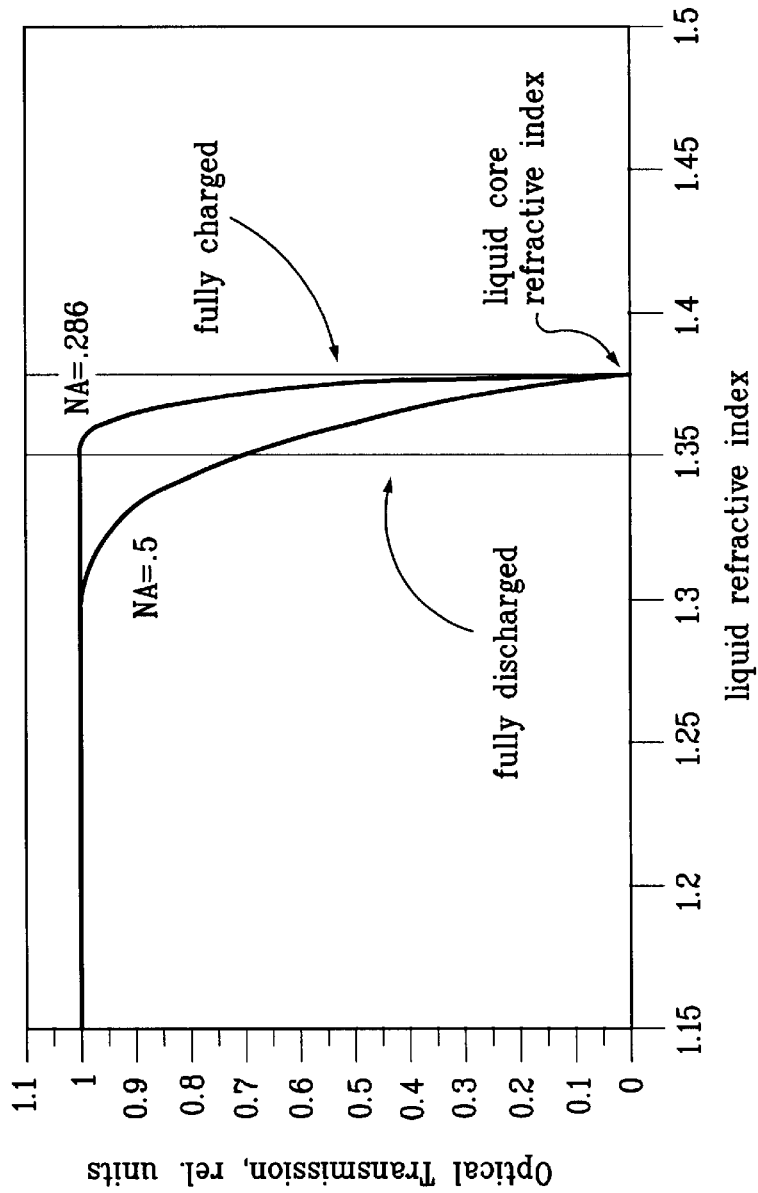

FIBER OPTIC REFRACTIVE INDEX MONITOR

The United States Government has rights in this invention pursuant to Department of Energy Contract No. DE-AC04-94AL85000 with Sandia Corporation.

BACKGROUND OF THE INVENTION

There are many examples of utilizing light through a optical waveguide to sense the change in refractive index of a liquid as an indication of the change in another characteristic of the liquid. For example:

U.S. Pat. No. 4,050,895, Sep. 27, 1977, of E. Hardy et al. discloses a cylindrical waveguide that is coated with a second material that reacts with the first material to be sensed. The reaction causes a change in color or other characteristic of the coating that effects the amount of light transmitted through the waveguide.

U.S. Pat. No. 4,187,025, Feb. 5, 1980, of A. Harmer discloses a short length of optical guideway having multiple bends that is immersed in a liquid under test. As shown in FIG. 6 of the '025 patent, a small change in the index of refraction of battery acid caused by a change in state of charge of the battery show a detectable change in contrast coefficient Γ for the multiple bend embodiments of FIGS. 3 and 4, and no change in contrast for the single bend structures of FIGS. 1 and 2.

U.S. Pat. No. 4,427,293, Jan. 24, 1984, of Harmer discloses a comparative system for compensating for the effect of temperature on the refractive index of liquids (typically, liquids have a temperature coefficient on the order of $-5 \times 10^{-4} / °C$).

J. Weiss, *Piezooptic behavior of certain fluids*, Applied Optics, Vol. 24, No. 8, 15 April 1985, pp. 1151–1155, shows in FIG. 9 curve 1(e) of this invention. This reference teaches that the refractive index of sensor fibers should be close the index of the liquid.

U.S. Pat. No. 4,851,817, Jul. 25, 1989, of C. Brossia et al. discloses a system for detecting ice or water on a surface with a short length of relatively straight optical waveguide with an external surface that has been abraded perpendicular to its axis. The device detects a relatively large change in index of refraction from 1 (for air) to 1.3 (for ice).

U.S. Pat. No. 5,141,310, Aug. 25, 1992, of A. Boiarski discloses a system for measuring the index of refraction of urine that has a multiple bend waveguide having a core refractive index that is greater than the index of high specific gravity urine (about 1.37), but not so great as to detract from accuracy and sensitivity. A preferred range is stated to be between 1.4 and 1.5.

SUMMARY OF THE INVENTION

It is an object of this invention to detect a small change in index of refraction of a liquid using a simple optical waveguide.

It is another object of this invention to detect a small change in index of refraction of a liquid by measuring the change in light through an optical fiber.

Additional objects, advantages, and novel features of the invention will become apparent to those skilled in the art upon examination of the following description or may be learned by practice of the invention.

To achieve the foregoing and other objects, and in accordance with the purpose of the present invention, as embodied and broadly described herein, the present invention may comprise a short straight length of optical guide having a smooth exterior surface along its length covered by a liquid, and a device for inputting a light beam into said guide. The angle of the light beam with respect to the optical guide and the index of refraction $n_g$ of the guide core is selected so that light impinges on the interface between the exterior surface and the liquid at the lowest critical angle of the guide. The critical angle changes as the index of the liquid changes such that after the change there is a detectable shift in the amount of light passing through the guide.

BRIEF DESCRIPTION OF THE DRAWINGS

The accompanying drawings, which are incorporated in and form part of the specification, illustrate an embodiment of the present invention and, together with the description, serve to explain the principles of the invention.

FIG. 2 shows a first embodiment of the invention utilizing an angled light input.

FIG. 4 shows a second embodiment of the invention utilizing a liquid-filled sensor.

FIG. 5 shows the transmission ratio for the embodiment of FIG. 4.

DETAILED DESCRIPTION OF THE INVENTION

A typical use for a sensitive liquid index of refraction detector is the detection of the state of charge of a lead-acid battery. The acid in a fully charged battery has a refractive index of approximately 1.38, while a discharged battery has a refractive index of approximately 1.35. A device that detects the state of charge based on refractive index of battery acid must be sensitive to less than a 3% change in the refractive index.

Those prior art devices that rely on multiple bend waveguides or abrasions for their operation are so constructed because the materials typically available for optical fibers, particularly plastic, have refractive indices considerably higher than the surrounding liquid to be monitored. Plastic has been emphasized for a variety of commercial applications because it is ductile and inexpensive. However, a typical plastic core of polymethyl methacrylate (PMMA) has a refractive index of 1.492. The fluorine-doped cladding of these fibers is about 1.417. If a straight length of such a sensor fiber is immersed in battery acid (where the liquid being sensed provides the cladding), the minimum light guiding capability (or numerical aperture) of the liquid-clad plastic sensor is so much higher than that of the fibers leading to it that the sensor fiber will guide all of the light entering it regardless of the value of refractive index of the surrounding liquid. Consequently, prior art straight sensors without bends or abrasions are totally insensitive to small changes in refractive index of surrounding liquids having refractive indices below 1.417.

Figure 1:
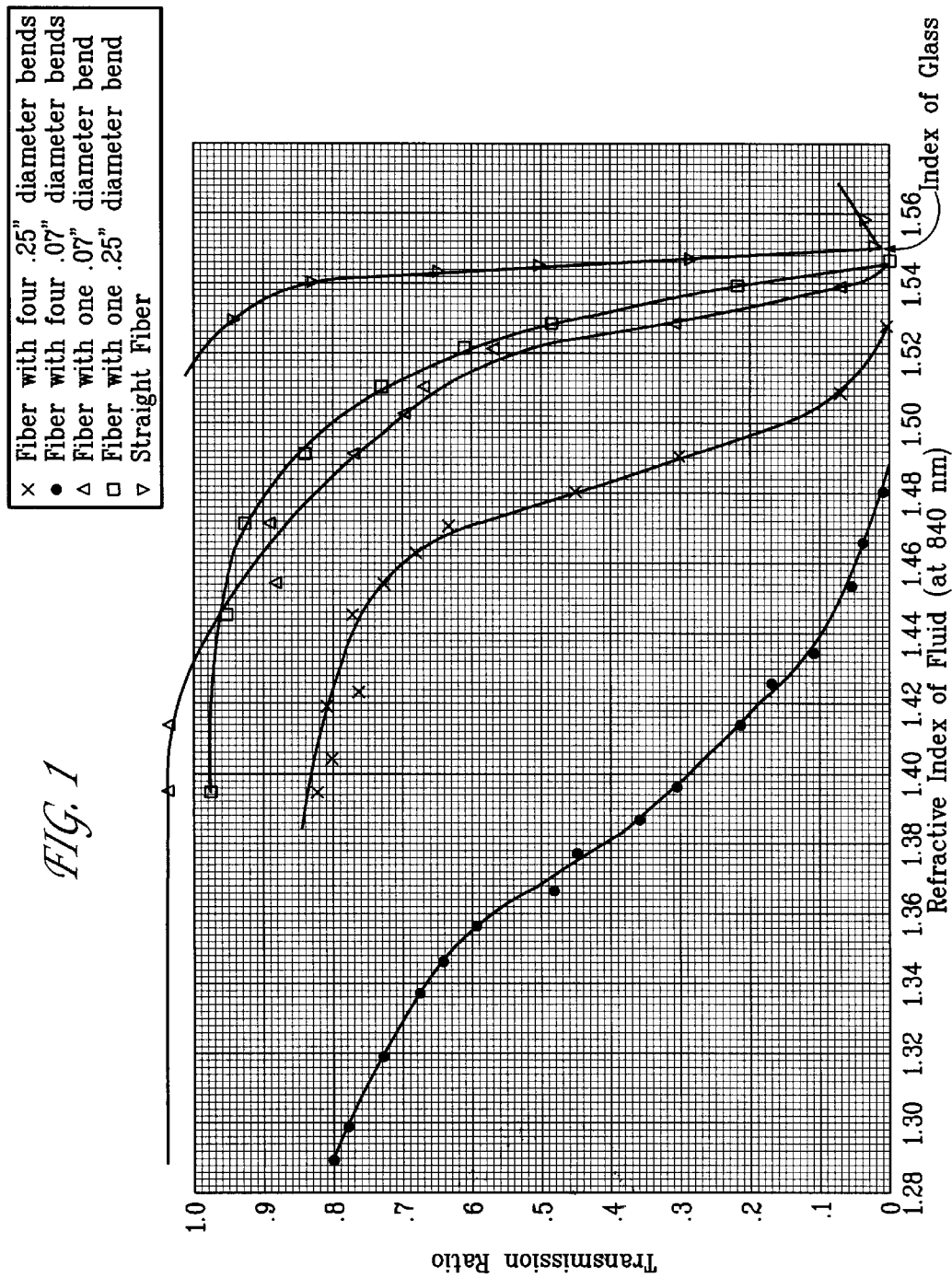
FIG. 1 shows transmission ratios for sensors with and without bends.

The basis of the aforementioned explanation is illustrated in FIG. 1, where the ratio of optical transmission through variously shaped glass fibers having a refractive index of 1.55 is illustrated as a function of the refractive index of the surrounding liquid. Curves a and b show multiply-bent fibers to have a relatively gentle slope; for curve a the transmission ratio changes from 0.4 to 0.6 as the liquid index changes from 1.38 to 1.35. Such a change could be detected electronically and be used for measuring the state of charge of a battery. However, the transmission ratio of the straight fiber, curve e, has a very steep slope and is at a maximum value for liquid indexes below 1.52. Such a fiber would be useless for indicating change between a liquid index of 1.38 and 1.35. However, if the zero transmission point of curve e could be placed at the highest value of liquid refractive index to be measured, then any slight change in liquid index would cause a significant change in transmission ration that would be easily detected. The problem has been that the zero transmission point of curve e corresponds to the refractive index of the fiber, and it is very difficult to get a fiber core having an index at the value of 1.38 required for measuring battery acid.

The numerical aperture of a fiber represents its light-gathering capacity and is defined as $NA=(n_{co}^2-n_{cl}^2)^{1/2}$ where co is "core " and cl is "cladding (or outside) ". It is well known that when light passes from an optical fiber of a given numerical aperture to another of a lower numerical aperture, a transmission loss occurs because the second fiber is not capable of guiding some of the higher-order modes, or large-angle rays, guided by the first. The size of the loss will depend upon the ratio of the numerical apertures and the distribution of optical energy among the modes of the fiber with the large NA. On the other hand, when light passes to a high numerical aperture, there will be no loss, regardless of the distribution of energy in the first fiber.

FIG. 2 shows a first embodiment of this invention to include a conventional straight optical fiber 10 a few centimeters long and on the order of 1 mm diameter which is immersed in a liquid 20. Fiber 10 may be made of PMMA having a refractive index of 1.492. Fiber 10 may also have a cladding 16 provided the cladding is thin compared to the fiber radius, as it is in conventional fibers. The cladding for such conventional fibers has no effect on meridional rays (those which pass through the center of the fiber), and an insignificant effect on the on internal reflection of all light at the intersection of the core and the liquid.

The input end 12 of fiber 10 is beveled at an angle θ from a plane normal to the axis of the fiber. This angle is calculated such that meridional light rays emerging from collimating lens 34 are refracted by the beveled surface 12 so that they impinge on the wall of fiber 10 at the "lowest critical angle " $\phi_c$. Light is provided to lens 34 through a conventional fiber 40 from a conventional light source 44.

Output end 18 of fiber 10 is coupled to an output assembly 50 that includes a reflector 52 having a conical depression 54 and an array of six receiving fibers 60 spaced around fiber 10. Reflector 52 is preferably a metal disk with depression 54 formed by the head of a drill bit. All fibers may be mechanically coupled to reflector 52 by epoxy, however, fibers 60 should be away from the outer surface of sensor 10 to allow fluid 20, and not epoxy or fibers 60, to provide the cladding for sensor 20.

In operation, the angle of depression 54 is designed so that the angled light emitted from fiber 10 reflects into output fibers 60. Light reflected from a flat reflector would enter the receiving fibers outside their numerical aperture and not be reliably guided by them. Conventional light detectors 62 at the other end of output fibers 60 provide a signal indicative of the amount of light transmitted through fiber 10, which signal correlates to the index of refraction of liquid 20.

Light transmission through fiber 10 is in accordance with Snell's Law, which defines the critical angle $\phi_c$, where sin $\phi_c$=(lower refractive index n')/(higher refractive index n), as the angle of incidence below which angle light passes through the interface, and above which angle light is reflected at the interface. The lowest critical angle $\phi_c$ is determined using the core of the optical fiber 10 and the lowest value to be detected of liquid 20. For this example, $\sin^{-1}(1.35/1.492)=64.8°$.

It is known from geometric considerations that skew rays, (those rays which do not pass through the center of the fiber but corkscrew around the axis during transit down the fiber) will impinge on the core boundary at a larger angle with respect to its normal than do meridional rays. Accordingly, if the meridional rays reflect, the skew rays reflect, and 100% of light is transmitted down the fiber. However, as the refractive index of the surrounding liquid 20 increases from its lowest value, the critical angle increases yet the angle of incidence remains at the lowest critical angle. The meridional rays now impinge upon the core boundary at too small an angle to be guided, and transmission decreases. As the critical angle continues to increase, more of the skew rays cease to be guided, and transmission further decreases. Thus, by launching the light into the fiber at the proper angle, rather than only the axis as is conventional, the fiber is sensitized to changes in the much-lower refractive index of the liquid, even though the numerical aperture of the liquid-clad fiber is much higher than that of its lead fiber.

Although the input light for FIG. 2 is illustrated as coming in parallel to the axis of fiber 10, it could also enter at an angle such as perpendicular to bevel 12. For any particular combination of type of fiber and type of fluid, it is a matter of routine calculation to determine the angle of bevel 12 so that when liquid 20 is at its lowest refractive index, light arrives at the interface at the lowest critical angle.

Figure 3:
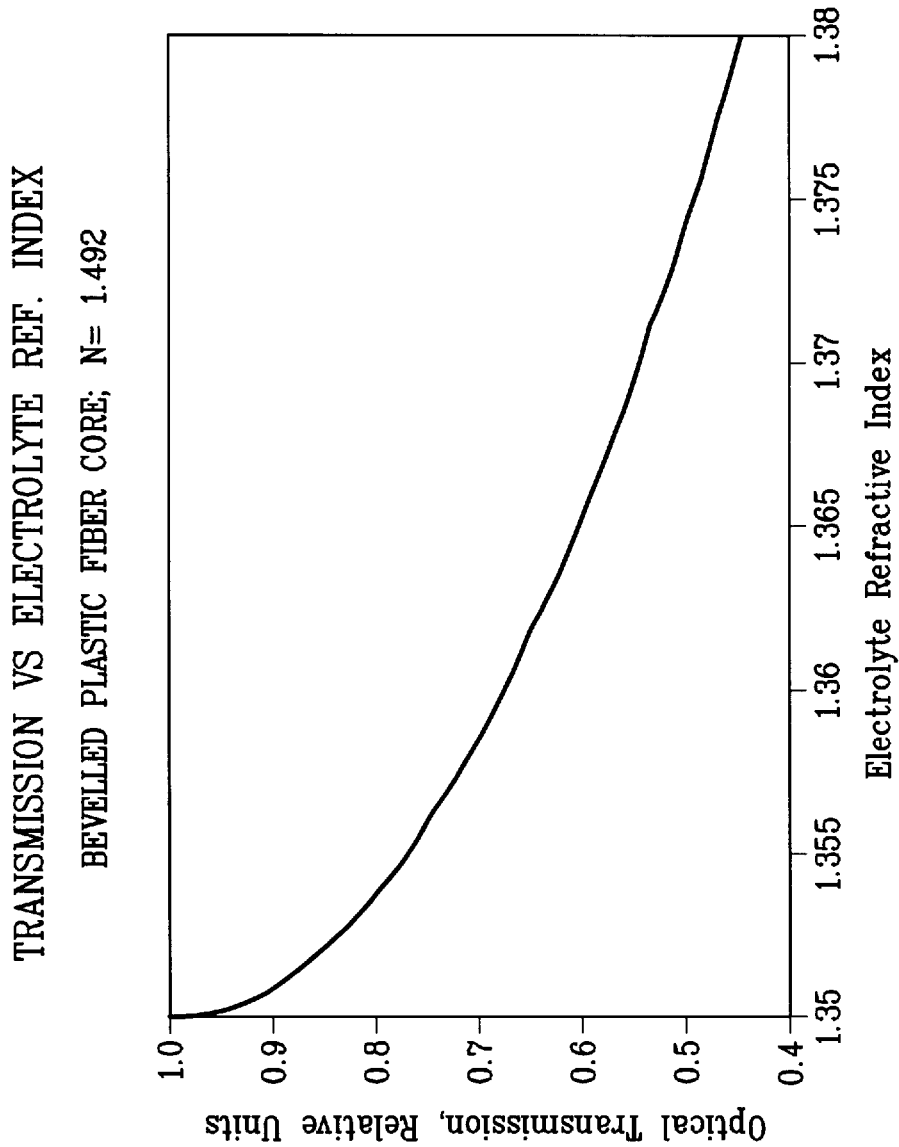
FIG. 3 shows the transmission ratio for the embodiment of FIG. 2.

FIG. 3 illustrates the results of a calculation involving a plastic fiber core and a liquid refractive index varying between 1.35 and 1.38, for perfectly collimated light from the lead fiber. The required bevel angle is 34.8°. It should be noted that the slope of this transmission curve is infinite at 1.35. Thus very small changes can be detected in refractive index in this vicinity. If the light is imperfectly collimated or the wrong bevel angle is used, then some of the light may be unaffected by the liquid refractive index over part or all of its range, or some may start out at less than perfect transmission. In either case, the total change in transmission will be less than the 55%, or so, of the "best performing sensor " shown in FIG. 3.

The embodiment of FIG. 2 provides sensitivity by changing the angle of the input light so that it hits the interface at the lowest critical angle when the liquid index is at its lowest value. The embodiment of FIG. 4 provides sensitivity by providing a sensor waveguide with a low refractive index so light in the highest order modes hits the interface at the lowest critical angle when the liquid index is at its lowest value.

As illustrated in FIG. 4, a short (on the order of a few cm), smooth (no abrasions or cuts on its exterior surface), straight (no bends) optical waveguide 11 with a refractive index $n_g$ immersed in a fluid 21 such as battery acid having a refractive index $n_l$ that changes by $\Delta n$ as some parameter of the liquid, such as its specific gravity, changes. Light from a source 45 is coupled to waveguide 51 through a clad input fiber 41; and light from waveguide 11 is coupled to a conventional detector 63 through clad output fibers 61. As in the first embodiment, output light is reflected from the output of guide 11 by a reflector 51 to output fibers 61. However, in this embodiment, light leaves waveguide 11 at a small enough angle that it will reflect from a flat surface and be guided by fibers 61.

For a liquid 21 with low enough refractive index, the resultant high NA for waveguide 11 ensures that it will receive all light from input lead 41. However, as the refractive index of liquid 21 increases, the NA for waveguide 11 decreases and eventually drops below the NA of input fiber 41. At this point a transmission loss occurs. As recognized by Weiss (cited above), if waveguide 11 is designed with index $n_g$ as close as possible to $n_l$, then the waveguide NA approaches zero and no light is transmitted to detector 61. However, light transmission will occur as the liquid index drops, and the waveguide NA increases.

The theoretical basis for that teaching is now known. A measurement of the angular spectrum of power from a fiber shows the resulting curve to closely match the function $\cos^2[\pi\theta]/2\sin^{-1}(NA)]$. FIG. 5 shows the result of a transmission calculation based on this function and plots the result as a function of the refractive index of the liquid cladding for input fibers 41 having NA values of 0.5 and 0.286. In this example, the core index is assumed to be 1.38, the upper value $n_g$ of liquid 21. There is no transmission of light when the liquid index is at that value. The lower the value of lead NA, the more steeply the slope of the curves as the index of the liquid decreases.

The ideal system for detecting a change in battery charge would have a sensor core index equal to the fully charged liquid index of 1.38, and lead fibers 41, 61 with an NA equal to the NA of guide 11 when the $n_i=1.35$. The resultant NA=0.286, a value that is attainable with plastic fibers. The resultant curve for such a fiber is shown in FIG. 5. With such a system, a change in liquid refractive index over the range being measured produces a change from 0 to 100% in transmitted light; a change which is easily quantified by conventional detector technology.

A problem with implementing such a system, and the problem that caused makers of other detectors to resort to multiple bends and abrasions on their waveguides, is that core materials with an index of refraction on the order of 1.38 are not readily available. A solution to this problem is the fluid-filled waveguide 11 of FIG. 4, where the waveguide is a transparent thin walled glass or plastic cylinder having flat end 17 optically connected to input fiber 41 by conventional coupling device 63 and output end 19. Waveguide 11 is filled with a fluid 15 having the desired reflective index at one end of the range of detection. For instance, it could be filled with battery acid from a charged battery having an index of 1.38. Because waveguide 11 is sealed after it is filled, fluid 15 is isolated from the physical changes caused by discharge of the battery or other similar event, and it remains at its original index of refraction as the index of fluid 21 changes. As with the clad fiber in the previous embodiment, if the walls of waveguide 11 are much thinner (less than 10%) than the radius of waveguide 11, they will have negligible effect on the reflections at the interface of the unchanged liquid 15 and measured liquid 21. It is contemplated that a waveguide according to this embodiment could have a diameter of approximately 1 mm, and a wall thickness of approximately of 50 microns.

While the NA of the output fiber is stated to be equal to the NA of the input fiber, it should be understood that the invention also contemplates using an output fiber having an NA greater than the NA of waveguide 11, as such a fiber will clearly transmit all light passing through waveguide 11 to detector 61.

The embodiment of FIG. 4 also addresses another problem; the effect of temperature change on this measurement. Since the liquid in sensor 31 is essentially the same as the liquid 21 being measured, any change in temperature will effect both liquids together. Any difference in refractive index between these liquids will thereby be caused by the physical parameter being sensed, and not an external change in temperature.

The particular sizes and equipment discussed above are cited merely to illustrate a particular embodiment of this invention. It is contemplated that the use of the invention may involve components having different sizes and shapes as long as the principle of using a sensor at the critical angle is followed. It is intended that the scope of the invention be defined by the claims appended hereto.

I claim:

1. A device for detecting a change $\Delta n$ in the index of refraction $n_l$ of a liquid between the values $n_l$ and $n_l - \Delta n$, comprising:

a short length of optical guide having refractive index $n_g$, said guide having a smooth exterior surface along its length covered by the liquid;

means for inputting a light beam into said guide,
        the angle of the light beam with respect to said optical guide being selected so that light impinges on the interface between said exterior surface and the liquid at the lowest critical angle $\phi_c$ of said guide, where $\phi_c = \sin^{-1}{(n_l - \Delta n)}/{n_g}$; and means for detecting the change in light passing through said guide.

2. The device of claim 1 wherein said guide is straight.

3. The device of claim 2 wherein the input end of said guide is beveled and light is input along the axis of said guide.

4. The device of claim 3 wherein said means for inputting a light beam comprises a first optical fiber having one end aligned with said optical guide and another end receiving light from a light source; and collimating means between said one end and said guide for collimating light entering said guide.

5. The device of claim 4 wherein said means for detecting the change in light passing through said guide comprises a second optical fiber having one end receiving light from said guide and another end for communicating light from said guide to a detector.

6. The device of claim 5 wherein said means for detecting further comprises means for reflecting light output of said guide to said second optical fiber.

7. The device of claim 1 wherein $\Delta n < (5\%)(n_l)$.

8. The device of claim 7 where $\Delta n < (5\%)(n_l)$.

9. A device for detecting a change $\Delta n$ in the index of refraction $n_l$ of a liquid between the values $n_l$ and $n_l - \Delta n$, comprising:

a short length of optical guide having a smooth exterior surface along its length covered by the liquid, said guide consisting of a thin walled container containing a liquid having an index of refraction $=n_l$;

means for inputting a light beam into said guide; and means for detecting the change in light passing through said guide.

10. The device of claim 9 wherein said means for inputting includes an optical fiber having one end aligned with an input end of said guide.

11. The device of claim 10 wherein said container is a cylinder.

12. The device of claim 11 wherein the diameter of said cylinder is approximately the same as the diameter of said fiber.

* * * * *